(12) United States Patent
Parmigiani (10) Patent No.: US 7,077,846 B2
(45) Date of Patent: Jul. 18, 2006

(54) DEVICE FOR WITHDRAWING FLAKES OR SHAVINGS FROM A DONOR BONE BY SCRAPING

(75) Inventor: Corrado Saverio Parmigiani, Correggio (IT)

(73) Assignee: C.G.M. S.P.A, Correggio (IT)

( * ) Notice: Subject to any disclaimer, the term of this patent is extended or adjusted under 35 U.S.C. 154(b) by 444 days.

(21) Appl. No.: 10/473,033

(22) PCT Filed: Feb. 1, 2002

(86) PCT No.: PCT/EP02/01162

§ 371 (c)(1),
(2), (4) Date: Sep. 26, 2003

(87) PCT Pub. No.: WO02/076307

PCT Pub. Date: Oct. 3, 2002

(65) Prior Publication Data

US 2004/0087959 A1 May 6, 2004

(30) Foreign Application Priority Data

Mar. 26, 2001 (IT) ............................. RE01A0028

(51) Int. Cl.
*A61B 17/14* (2006.01)
(52) U.S. Cl. ....................................................... 606/84
(58) Field of Classification Search ................. 606/79, 606/84, 85, 86, 114, 115, 127, 128, 170, 167
See application file for complete search history.

(56) References Cited

U.S. PATENT DOCUMENTS

| 4,243,048 | A | * | 1/1981 | Griffin ........................ 600/564 |
| 5,250,061 | A | | 10/1993 | Michelson |
| 5,387,215 | A | | 2/1995 | Fisher |
| 5,683,406 | A | | 11/1997 | Altobelli et al. |
| 6,110,177 | A | | 8/2000 | Ebner et al. |
| 6,755,837 | B1 | * | 6/2004 | Ebner ........................ 606/84 |

FOREIGN PATENT DOCUMENTS

DE 83 13 370 9/1983

* cited by examiner

*Primary Examiner*—Eduardo C. Robert
*Assistant Examiner*—James L Swiger
(74) *Attorney, Agent, or Firm*—Browdy and Neimark, PLLC

(57) ABSTRACT

A device for withdrawing flakes or shavings from a donor bone by scraping, comprising an internally hollow handle composed of a hollow body with a cavity and of a slidable closure, rendering the cavity accessible, respectively. The scraper is positioned at the front end of the slidable closure and has a gap for the passage of bone flakes or shavings into the cavity. The scraper also comprises a blade positioned at the front end of the slidable plate, and has an active surface perpendicular or nearly perpendicular to the longitudinal axis of the front portion of the handle. The slidable closure comprises an upper plate, positioned at the upper side of the hollow body to close the cavity and slidable on this latter portion, its front portion not joined to the hollow body and being elastically deformable to move away from the front edge of this latter portion when under load.

11 Claims, 7 Drawing Sheets

DEVICE FOR WITHDRAWING FLAKES OR SHAVINGS FROM A DONOR BONE BY SCRAPING

TECHNICAL FIELD

The present invention relates to the surgical technique of bone transplant, and in particular the withdrawal of bone fragments from a donor bone and their transplanting into a receiver bone which is to be at least partially reconstructed.

More precisely, the invention relates to the withdrawal of small particles of healthy bone in the form of shavings or flakes, to be transplanted into the tissue to be reconstructed, especially in facial and dental jawbone surgery.

The withdrawal is preferably effected on a bone of the same patient, the withdrawn material being used to induce the re-growth of bone where this is lacking either because of natural causes (atrophies) or because of provocation (traumas), or to regenerate bone defects during reconstruction, or again to enlarge weakened bone sections.

The problem confronted by the present invention is to withdraw and transfer bone flakes or shavings.

The material must be withdrawn without causing any damage to the bone itself or to the soft parts surrounding the area of intervention. It is therefore of fundamental importance that the withdrawal concerns only the cortical part of the bone, without intervening on its medullary or spongy part. A further requirement is to collect the withdrawn bone scales or shavings and to preserve them until their grafting into direct contact with the defective bone to be regenerated.

The final requirement is to render the withdrawal device inoffensive after use. In this respect, once used it becomes potentially infected by its contact with blood and bone material, and must therefore be protected to prevent the operator or the device disposal personnel being accidentally wounded, with serious danger of infection.

BACKGROUND ART

Although the available state of the art devices have proved suitable for the purpose, they present defects and limitations which need to be eliminated. Devices are known, illustrated in U.S. Pat. No. 5,683,406, comprising a cutting edge positioned on the front side of a half moon-shaped aperture provided at the end of a slidable plate which closes a cavity in a handle, the purpose of which is to collect the shavings.

The cutting edge of said half moon-shaped aperture emerges on that side of the plate external to said cavity, and remains accessible from the outside in any position of the plate.

The handle cavity is closed by a slidable plate which uncovers the aperture for collecting the shavings which are formed by bringing said cutting edge into contact with the donor bone and sliding it along this latter while maintaining it pressed with a certain force.

This type of device presents a first defect deriving from the fact that the curved shape of the cutting edge intended to operate as a scraper makes it difficult to guide the instrument along the bone, in the sense that the cutting edge tends to deviate to the right or to the left of the path chosen by the surgeon.

Secondly, the pressure with which the cutting edge acts is determined essentially by the surgeon, with the double danger that the instrument may escape from his hand with the evident risk of cutting or lacerating the soft tissue close to the withdrawal region, and that excessive pressure may cause serious undesirable injury to blood vessels or, more dangerously, to nerves or tendons.

Finally, once used the device must be protected, because its cutting part remains exposed and can therefore accidentally wound whoever comes into contact with it, with the risk of infection.

An object of the invention is to eliminate said problems within the framework of a simple and economical construction.

DISCLOSURE OF THE INVENTION

Said object is attained by a device having the characteristics defined in the claims.

It is composed of an internally hollow elongate handle of any cross-section of suitable shape, consisting of a hollow body having a cavity, the upper face of which is closed by a slidable plate which closes and renders accessible the cavity and has its front end not joined to the hollow body and elastically deformable so that it moves away from the front edge of this latter when under load; at its front end, said slidable plate carries a blade having an active surface perpendicular or nearly perpendicular to the longitudinal axis of the front portion of the handle, and having its cutting edge of arcuate profile to act as a scraper the cutting or scraping edge of which is directed towards the hollow body and projects downwards from it.

The front end of the hollow body is shaped such that while maintaining its width unaltered, it degrades in height until it reaches the cutting edge of the blade, which has a rounded surface to rest on the donor bone.

The slidable plate is secured to the hollow body by slidable connection means provided with stops which when the plate is in its maximum advancement position allow the blade to just project beyond the edge of the curved surface of the hollow body, whereas when the plate is retracted its position is such that the cutting edge of the blade is inaccessible from the outside.

At that end close to the curved surface of the body the plate connection means terminate at a certain distance from the front edge of said surface such that that portion of the plate which terminates with the blade is projectingly supported elastically.

The materials of construction of the device are not critical, except for the blade which obviously has to be of steel, and for the slidable plate which has to have a certain elasticity.

Preferably both the hollow body and the slidable plate are constructed of synthetic resin suitable for medical use, such as polycarbonate or acrylonitrile/butadiene/styrene.

The merits and the operational and constructional characteristics of the invention will be apparent from the ensuing detailed description relative to a preferred embodiment thereof given by way of non-limiting example and illustrated by the figures of the accompanying drawings.

The device of the invention comprises an internally hollow, elongate handle M of variable cross-section and suitable shape, comprising a hollow body 1 defining a cavity 11, the upper face of which is closed by an upper plate 6 slidable on the hollow body 1, to close and alternately render accessible the cavity 11 thereof; a blade 20 is positioned at the front end of the upper plate 6.

The hollow body 1 presents a rounded front portion 2 in which the cavity 11 is provided, and a flat intermediate portion 3 positioned adhering to the plate 6.

On the side walls of the hollow body 1 there are provided two respective longitudinal ribs 4 projecting radially outwards from the surrounding surface and extending in a longitudinal direction, to slidingly engage respective longitudinal seats 5 provided on the sides of the upper plate 6 in order to form a connection which retains the plate 6 in contact against the hollow body 1 and enables it to slide relatively in a longitudinal direction. The mutual connection means 4 and 5 are such as to enable the upper plate 6 to slide on the hollow body 1, in a longitudinal direction, between a forward end position (closed position) and a retracted position (open position). When the plate 6 is in its forward end position, its front portion 7 faces and is in contact with the front portion 2 of the hollow body 1, to close its cavity 11. In contrast, when in its retracted position, the cavity 11 is totally or partly uncovered.

The ribs 4 are present on that part of the body 1 to the rear of the front portion 2 and terminate where this portion 2 commences; at that point they present two end stop teeth 8 which limit the travel of the plate 6. Likewise the longitudinal seats 5 are present on that part of the plate 6 to the rear of the front portion 7 and terminate where this portion 7 commences.

Figures 1, 2:
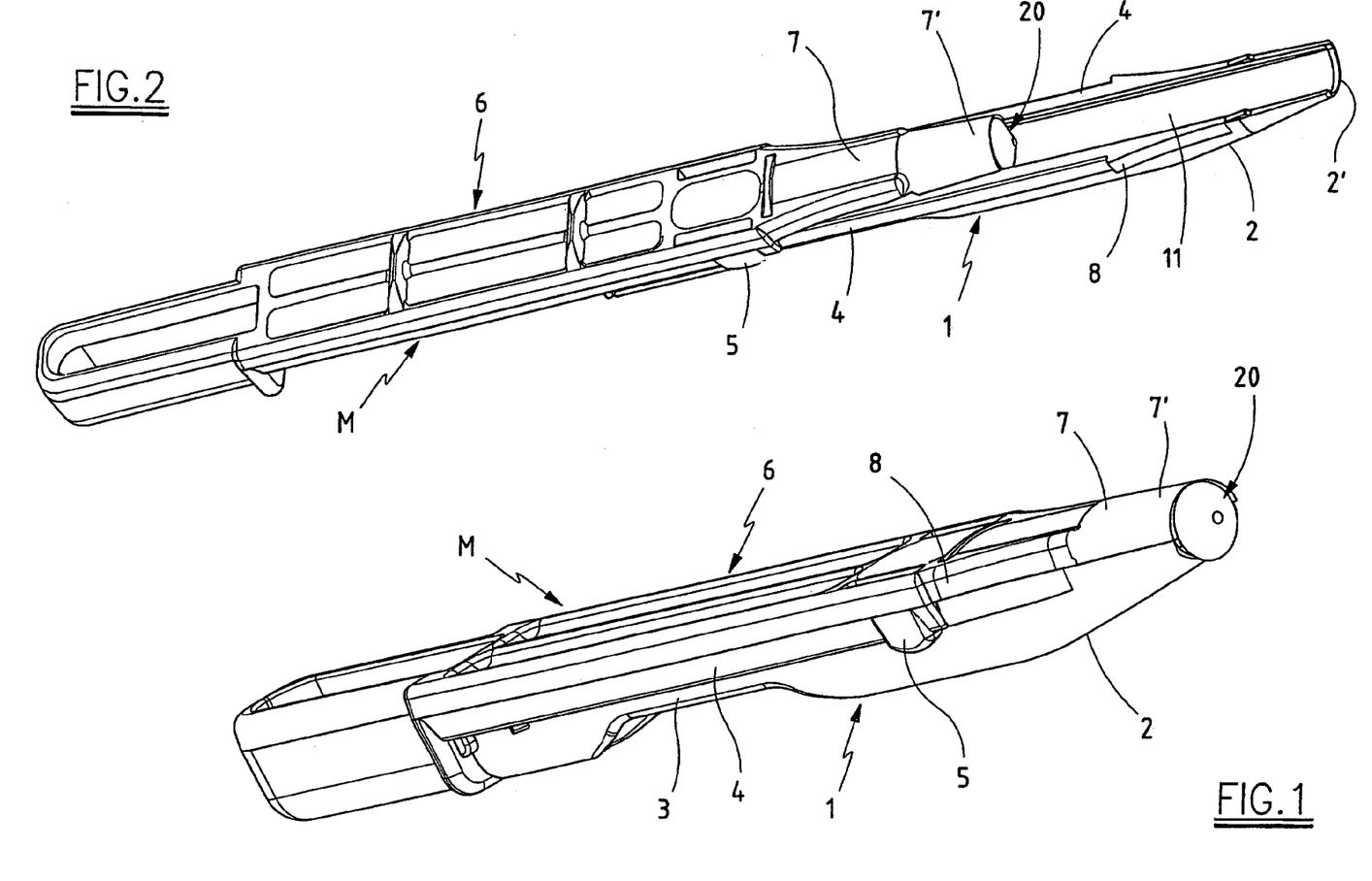
FIG. 1 is a three-quarter perspective view from above, showing the device of the invention in the closed position.
FIG. 2 is another perspective view from a slightly displaced viewing point, showing the same device in the open position.
Figure 3:
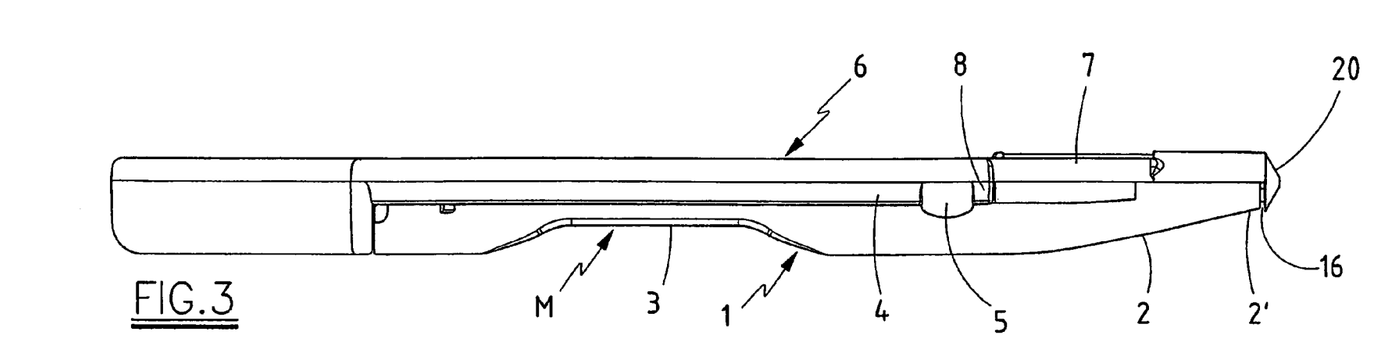
FIG. 3 is a side view of the device in the closed position.
Figure 4:
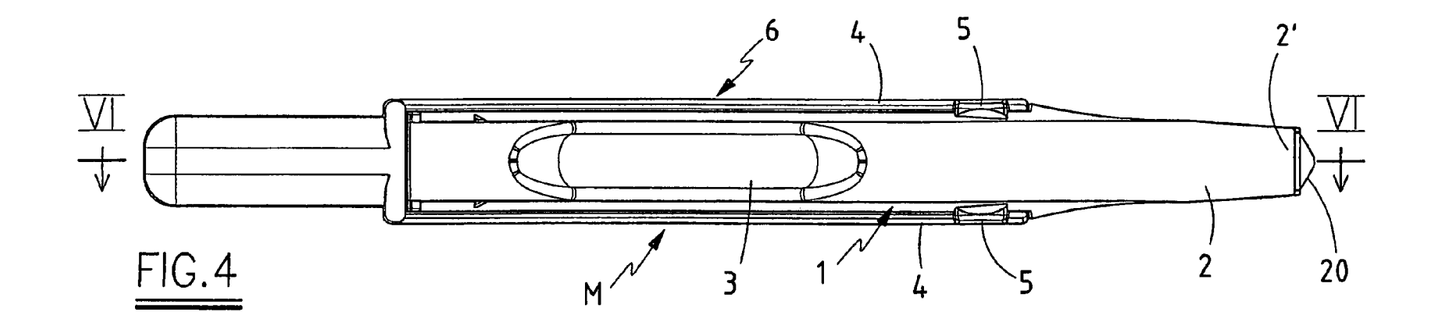
FIG. 4 is a plan view from below showing the device in the closed position.
Figure 5:
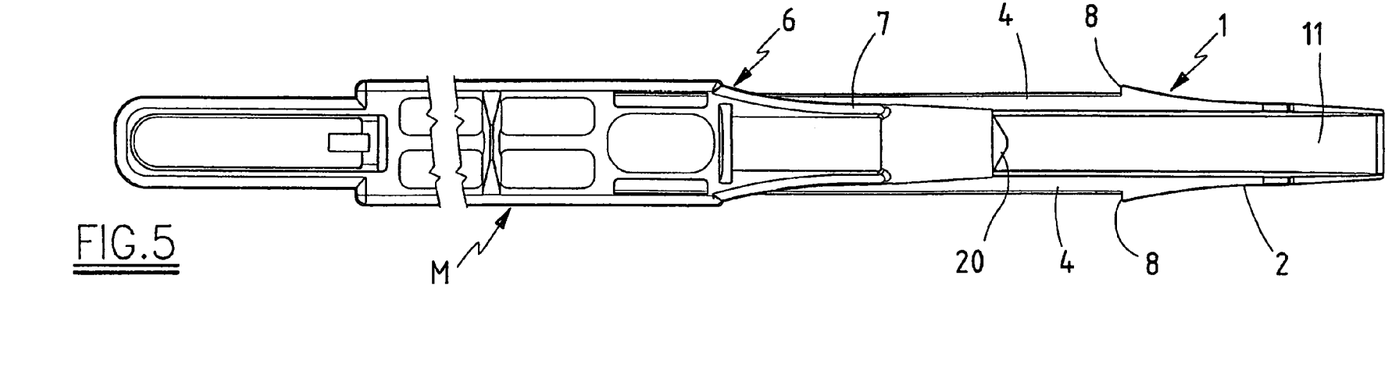
FIG. 5 is a plan view from above showing the device in the open position.
Figure 6:
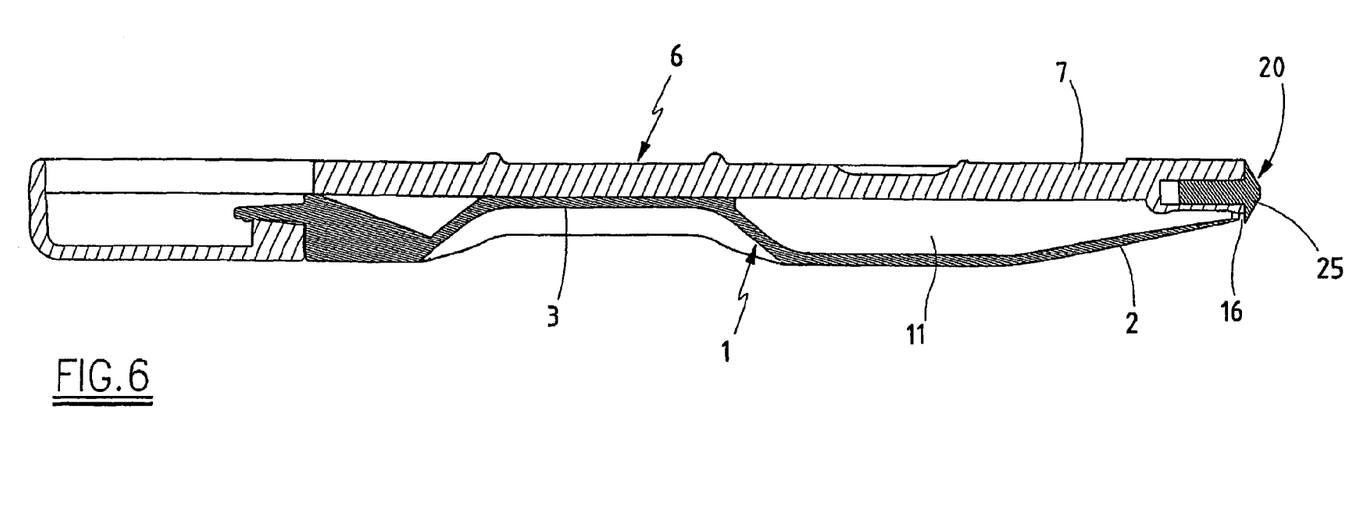
FIG. 6 is a section on the plane VI—VI of FIG. 4.
Figure 6A:
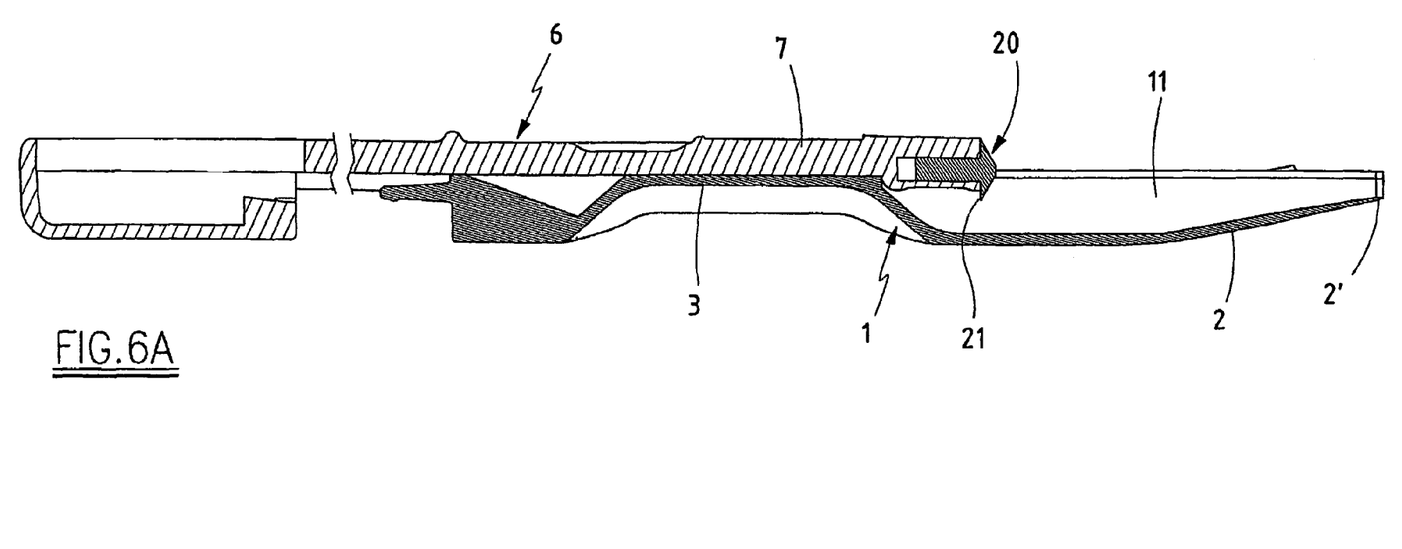
FIG. 6A shows the same section as FIG. 6, but with the device in the open position.

Consequently, when the plate 6 is in the closed position as in FIG. 6, the front portion 7 of the upper plate 6 projects beyond the stop teeth 8 and is released from the hollow body 1 (it is projectingly supported elastically by the ribs 4 and only rests on the body 1); it is also elastically deformable so that it can bend to rise in a transverse direction, when under load, from the front edge 2' of the hollow body 1.

To the front end 7' of the front portion 7 there is fixed a steel blade 20 having an active surface 21 perpendicular or nearly perpendicular (i.e. forming an angle of about 80–100 degrees) to the longitudinal axis of the front portion of the upper plate 6, and having its cutting edge of arcuate profile, to act as a scraper the cutting or scraping edge of which is directed towards said hollow body and projects downwards therefrom.

Specifically, the blade 20 is formed from a truncated cone 25, of which the axis is parallel to the longitudinal axis of the front portion of the hollow body 1, and the vertex faces forwards; its major base is flat or nearly flat, and defines said active surface 21; the edge of its major base is circular and forms a cutting edge 22 the lower portion of which is arranged to scrape along the donor bone. The height of the truncated cone 25 is evidently much smaller than the diameter of the major base, so that the angle (defining the cutting edge 22) formed, in the axial section, between the active surface 21 and the conical surface is quite small and pointed.

The truncated cone 25 is joined to an axial rod 26, which extends from the surface 21 and is fixedly inserted into the front end 7' of the plate 7, with its axis parallel to the longitudinal axis of the front portion of the handle M.

When the plate 6 is in the closed position, as in FIG. 6, the blade 20 projects axially forwards beyond the front end edge 2' of the hollow body 1, and the lower part of the cutting edge 22 projects slightly downwards beyond the same end edge 2' of the body 1. When the plate 6 is in the open position, the cutting edge 22 of the blade is not accessible from the outside.

Figure 7:
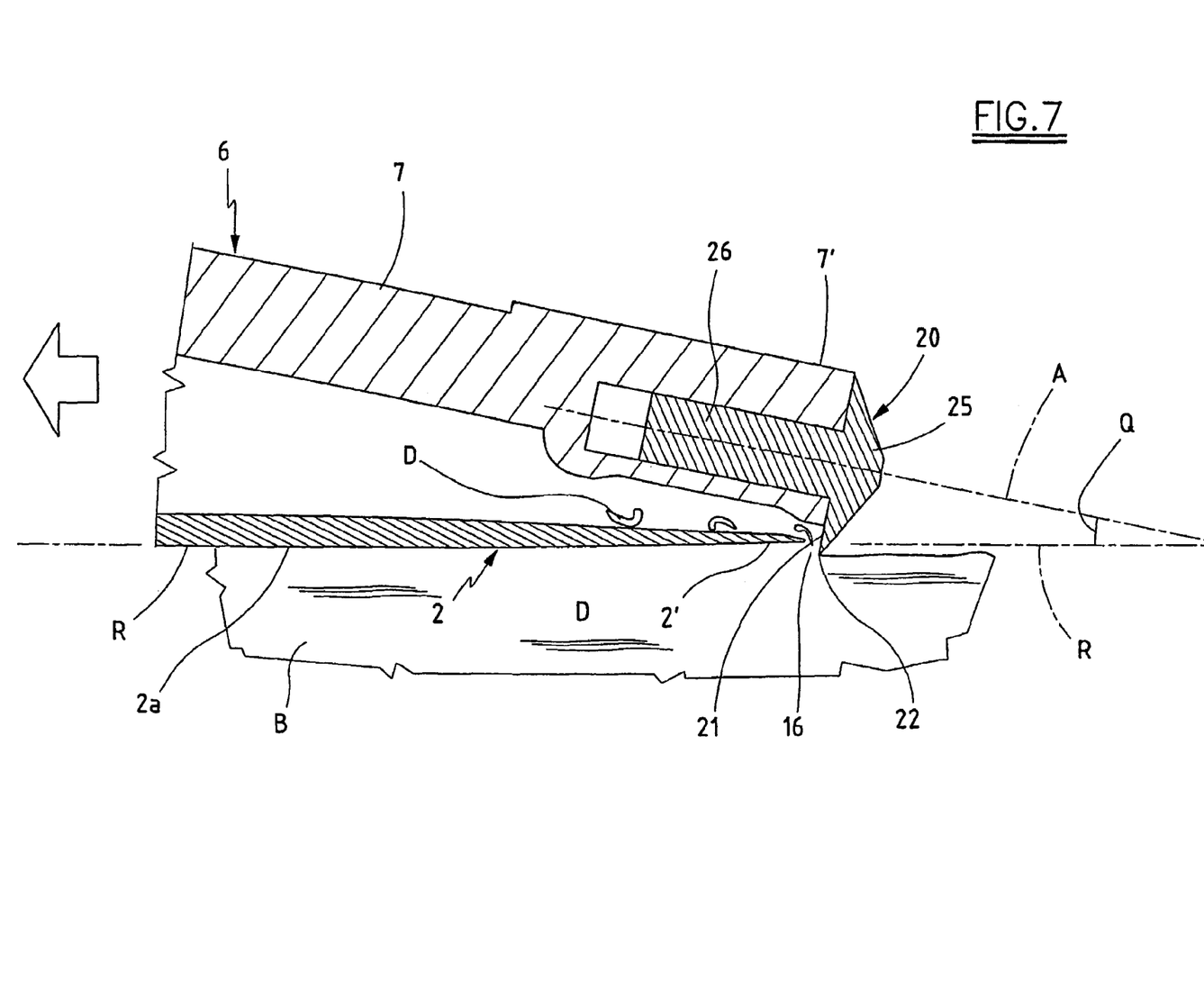
FIG. 7 is an enlarged detail of FIG. 6, showing the front end of the device during scraping.
Figure 8:
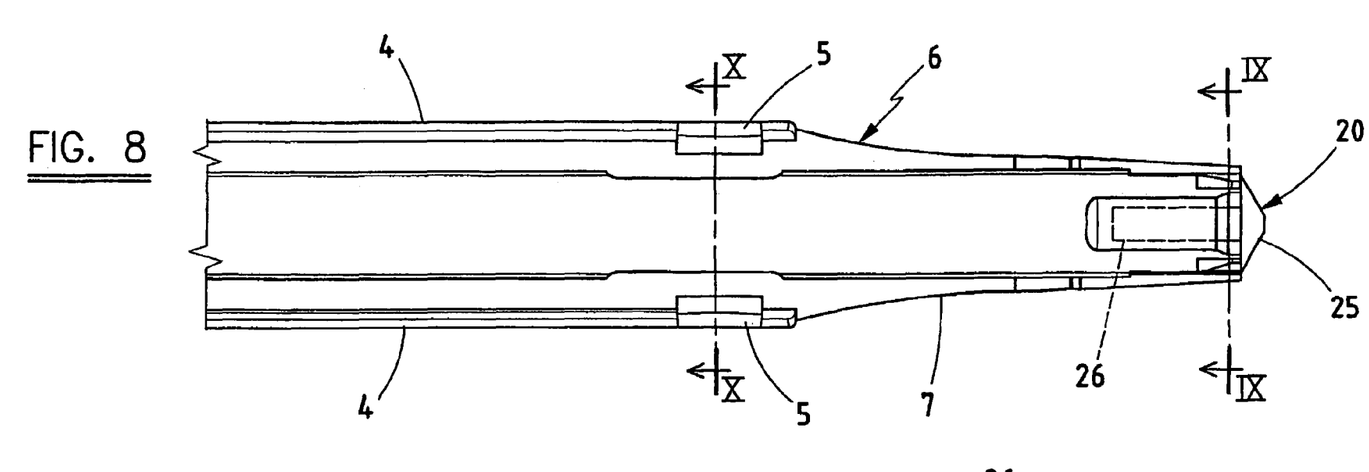
FIG. 8 is a plan view from below, showing just the upper plate 6 of FIG. 7.
Figure 9:
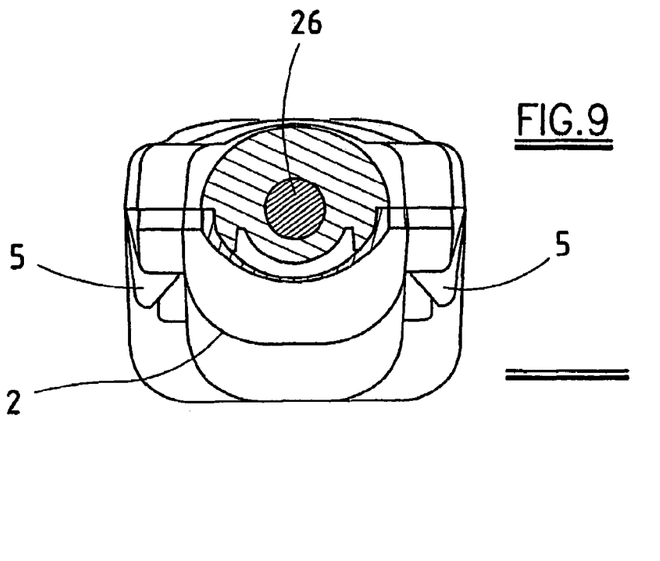
FIG. 9 is a section on the plane IX—IX of FIG. 8.
Figure 10:
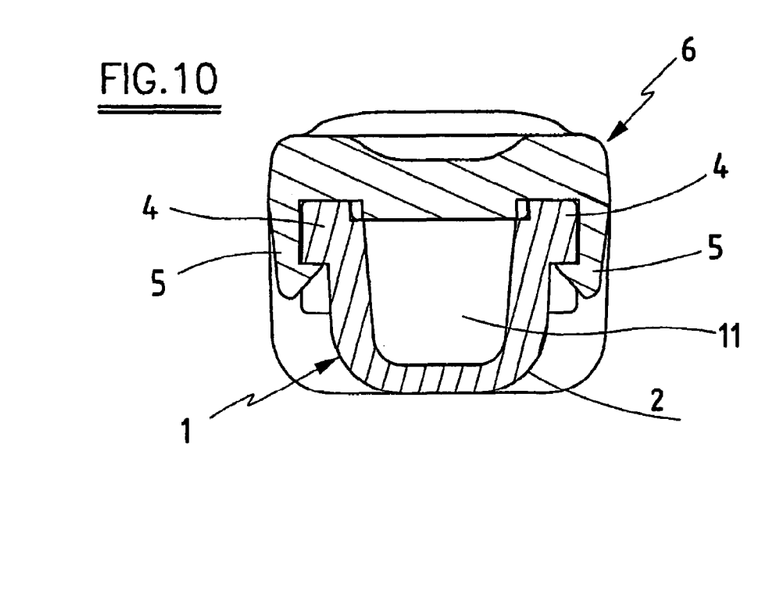
FIG. 10 is a section on the plane X—X of FIG. 8.

The front end edge 2' of the hollow body is positioned a short distance, in a radial direction, from the lower surface of the front end 7' of the upper plate 6 and also a short axial distance to the rear of the blade 20 to define, when the front portion 7 of the plate 6 is bent upwards, a narrow gap 16 for the passage of the bone flakes or shavings D towards the interior of the cavity 11 in the hollow body (FIG. 7).

When in operation, the device of the invention is used in the closed position for scraping. Typically, a force is applied to the device towards the bone B, and the front part 2 of the hollow body 1 is positioned such that it adheres to and rests on the surface of the bone B. Alternatively, the front part 2 can form an angle with the surface of the bone B and rest on it only with its end edge 2'. As the cutting edge 22 projects downwards from the end edge 2' of the body 1, it comes into contact with the donor bone and urges the front portion 7 upwards so that it bends to separate from the body 1 and form said gap 16, which is about 0.5 mm wide. At the same time, the cutting edge 22 is pressed against the bone with a substantially constant force, determined by the reaction to the elastic deformation of the portion 7. By moving the device parallel to the surface of the bone B, the blade 20 acts with its active surface 21 to produce shavings or flakes D which by virtue of the action of the active surface 21 are collect in the cavity 11 via the gap 16.

The constant thrust with which the cutting edge 22 is pressed avoids the danger of cutting or lacerating soft tissue close to the withdrawal region, caused by excessive pressure, which could cause serious undesirable injury to blood vessels or, more dangerously, to nerves or tendons.

The deformation of the front portion 7 hence slightly distances the front edge 2' of the hollow body 1 from the end 7' of the plate 6, to increase the passage gap 16 for the bone shavings which enter the hollow body and are collected therein and preserved.

The front portion 2 of the hollow body 1 is shaped such that although it maintains its length unaltered, it degrades in height to reach zero at the cutting edge 22 of the blade. Specifically, the lower profile (indicated by R in FIG. 7) of the lower surface 2a of the front portion 2 forms with the axis A of the blade 20, an acute angle Q in the axial plane having a size of 5–30 degrees, i.e. such that whereas the profile R substantially adheres to the surface of the bone B during scraping, the active surface 21 of the blade 20 is inclined to the vertical at the surface of the bone B by a corresponding acute angle suitable for scraping shavings and flakes D from the bone B. This characteristic substantially improves the performance of the instrument.

Moreover, the front portion 2 of the hollow body 1 presents at its front end a rounded lower surface 2a suitable for resting on the donor bone.

By then pulling the upper plate 6 rearwards, the cavity 11 is uncovered to enable the accumulated bone particles to be extracted therefrom.

At that end distant from the rounded end, the cavity 11 in the hollow body 1 terminates with a flat intermediate portion 3 lying substantially in contact with the upper plate 6, and of sufficient length such that, when the upper plate 6 is retracted completely, the cutting edge 22 of the blade lies on said flat part to remain protected from accidental contact.

Figure 11:
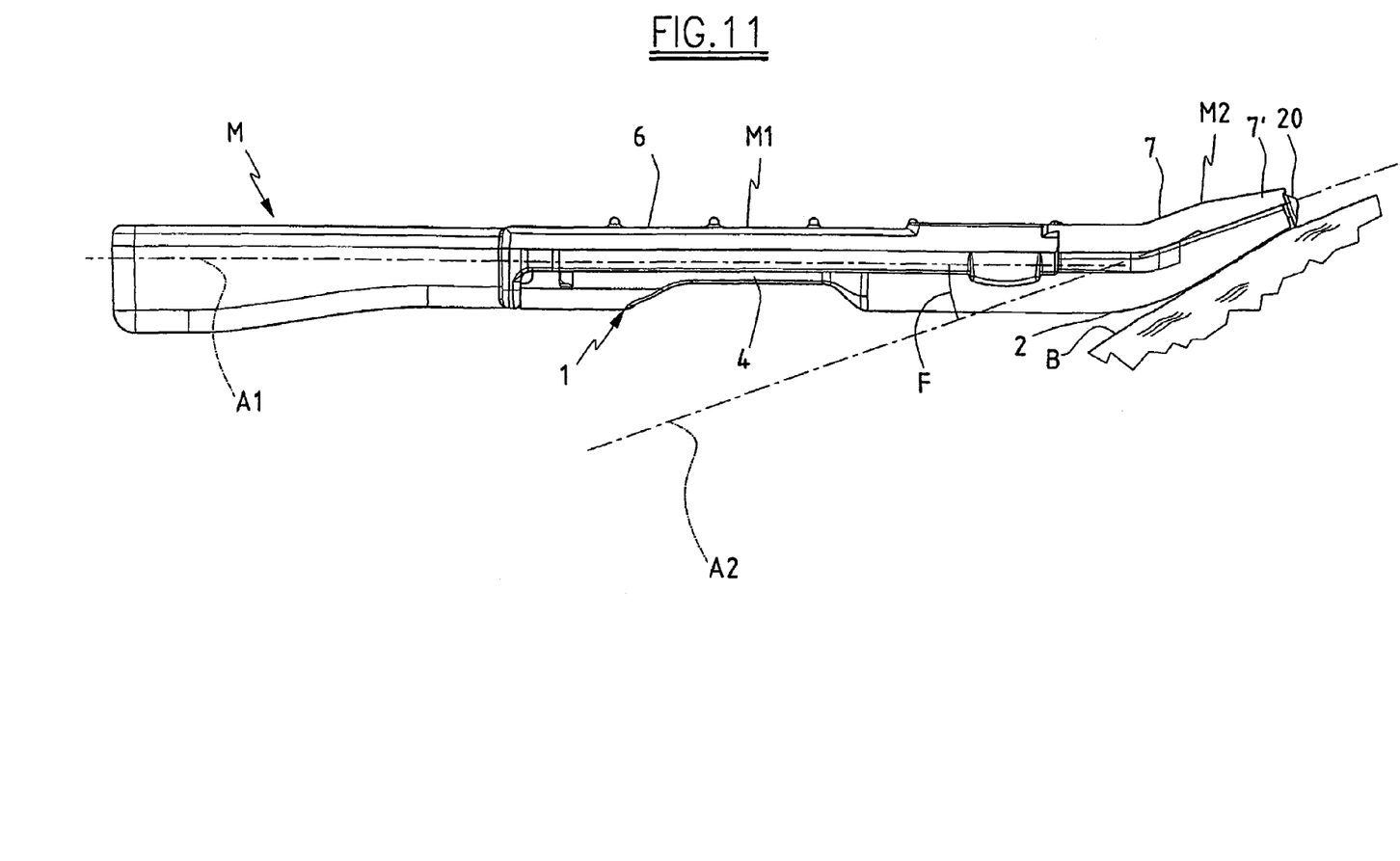
FIG. 11 is a side view of a second embodiment of the invention.
Figure 12:
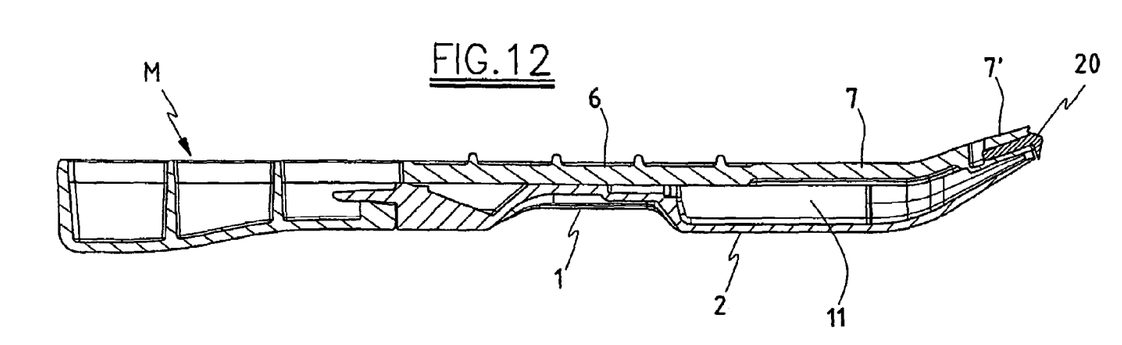
FIG. 12 is a section on the longitudinal plane of symmetry of FIG. 11.
Figure 13:
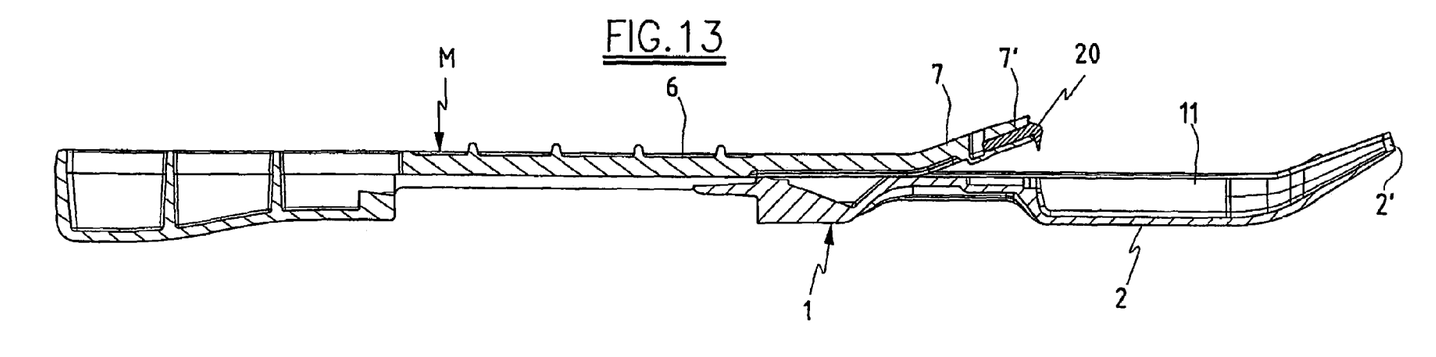
FIG. 13 shows the same section as FIG. 12, but with the device in the open position.

The embodiment shown in FIGS. 11, 12 and 13 differs from the preceding illustrated embodiment in that the handle M comprises a front portion M1 of longitudinal axis A1, which carries the blade 20, and a rear portion M2 of longitudinal axis A2, to be gripped by the operator.

The longitudinal axes of the two portions M1 and M2 form a contained angle F, for example of 15–25 degrees to determine an ergonomic shape.

The angle F can be on one or other side with respect to the axis A2.

The invention claimed is:

1. A device for withdrawing flakes or shavings from a donor bone by scraping, comprising:
   an internally hollow handle (M) comprising a hollow body (1) with a cavity (11) for collecting bone and means for closing the cavity (11), and
   scraper means (20) having a cutting edge (22), the lower portion of which is arranged to scrape along the bone; characterised in that said means for closing the cavity (11) is positioned on the upper side of the hollow body (1) to close the cavity (11) and the scraper means (20) is positioned at the front end of said means for closing the cavity (11), projecting axially forwards beyond the front end edge (2') of the hollow body (1),
   the lower part of the cutting edge (22) projecting radially downwards beyond the same end edge (2') of the body (1) and providing a gap for passage of the bone flakes or shavings between the said cutting edge (22) and the front end edge (2') of the hollow body (1).

2. A device as claimed in claim 1, characterised in that said scraper means comprise a blade (20) positioned at the front end of a slidable portion (6), and having an active surface (21) perpendicular or nearly perpendicular to the longitudinal axis of the front portion of the handle (M).

3. A device as claimed in claim 2, characterised in that the profile of the cutting edge (22) of the blade (20) is arc shaped.

4. A device as claimed in claim 3, characterised in that the blade (20) is in the form of a truncated cone, with its axis (A) parallel to the longitudinal axis of the front portion of the hollow body (1) and its major base flat or nearly flat to define said active surface (21) of the blade (20) with its edge forming a cutting edge (22), the lower portion of which is arranged to scrape along the donor bone.

5. A device as claimed in claim 1, characterised in that the front end edge (2') of the hollow body (1) is positioned at a short distance from the lower surface of the front end (7') of the upper plate blade (6) in a radial direction, and also a short axial distance to the rear of the blade (20), to define, when the front portion (7) of the plate (6) is bent upwards, a narrow passage for the bone flakes or shavings (D) towards the interior of the cavity (11).

6. A device as claimed in claim 5, characterised in that the connection means (4, 5) between the hollow body (1) and the upper plate (6) terminate at a certain distance from the front edge (2') of the hollow body (1) such that the front portion (7) of the plate where the blade (20) is positioned is projectingly supported elastically.

7. A device as claimed in claim 6, characterised in that said handle (M) comprises a front portion (M1) which carries the blade (20), and a rear portion (M2) to be gripped by the operator, said portions (M1 and M2) having longitudinal axes (A1, A2) which form a contained angle F to define an ergonomic shape.

8. A device as claimed in claim 1, characterised in that the front portion (2) of the hollow body (1) is shaped such that it degrades in height to its front end (2') to reach zero at the cutting edge (22) of the blade, where it has a rounded lower surface (2a) to rest on the donor bone.

9. A device as claimed in claim 8, characterised in that the upper plate (6) is secured to the hollow body (1) by lateral connection means (4, 5) such that it can slide relative thereto, in a longitudinal direction, between a forward end position, in which it closes the cavity (11) of the hollow body (1) and the blade (20) projects forwards beyond the front end edge (2') of the hollow body (1), and a retracted position in which the cavity (11) is at least partially uncovered and the cutting edge (22) of the blade (20) is inaccessible from the outside.

10. A device as claimed in claim 1, characterised in that the lower profile (R) of the lower surface (2a) of the front portion (2) forms with the axis (A) of the blade (20), in the axial plane, an acute angle (Q) of 5–30 degrees in size.

11. A device as claimed in claim 1, characterised in that said means for closing the cavity (11) comprises an upper plate (6) positioned on the upper side of the hollow body (1) to close the cavity (11), its front portion (7) being not joined to the hollow body (1) and being elastically deformable to move away from the front edge of this latter when under load.

* * * * *